United States Patent [19]

Lindemann et al.

[11] Patent Number: 4,787,397
[45] Date of Patent: Nov. 29, 1988

[54] HOT AND COLD SENSOR DISCRIMINATION UNIT

[75] Inventors: Peer Lindemann, West Bend; Robert R. Ungemach, Brown Deer, both of Wis.

[73] Assignee: Smith & Nephew Rolyan, Inc., Menomonee Falls, Wis.

[21] Appl. No.: 60,463

[22] Filed: Jun. 11, 1987

[51] Int. Cl.[4] .............................................. A61B 5/00
[52] U.S. Cl. .................. 128/742; 128/736; 374/204
[58] Field of Search .............................. 128/742, 736; 374/157–158, 204

[56] References Cited

U.S. PATENT DOCUMENTS

| 2,536,001 | 12/1950 | Chase | 128/742 |
| 2,572,059 | 10/1951 | Schlaich | 374/204 |
| 2,645,097 | 7/1953 | Posch | 128/742 |
| 2,981,108 | 4/1961 | Andersen et al. | 374/158 X |
| 3,533,397 | 10/1970 | Scher | 128/742 X |
| 4,026,275 | 5/1977 | Jablecki | 128/742 |
| 4,292,979 | 10/1981 | Inglefield et al. | 128/743 |

FOREIGN PATENT DOCUMENTS

| 2609415 | 9/1977 | Fed. Rep. of Germany | 128/742 |
| 2585232 | 1/1987 | France | 128/742 |

Primary Examiner—Kyle L. Howell
Assistant Examiner—Angela D. Sykes
Attorney, Agent, or Firm—Ira Milton Jones

[57] ABSTRACT

A hot and cold sensor discrimination unit having an insulated liquid-filled container with a temperature indicator and a metal probe with a temperature indicator for use in perception of temperature by a patient.

11 Claims, 2 Drawing Sheets

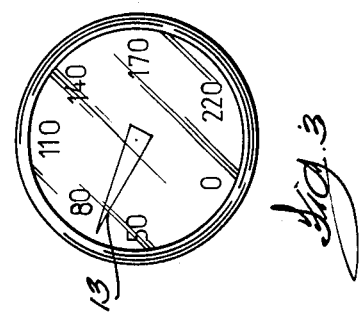
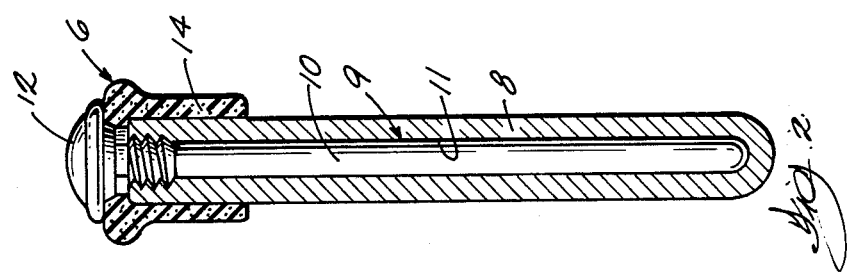
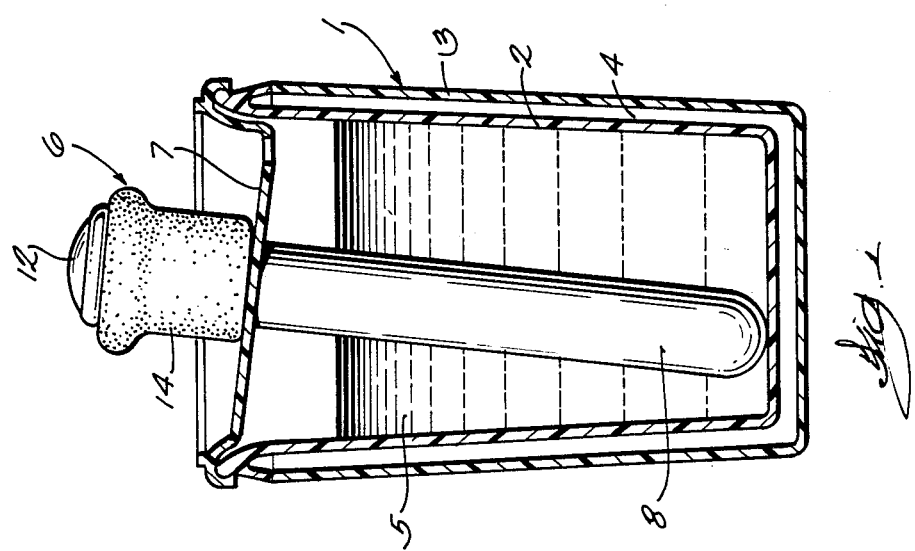

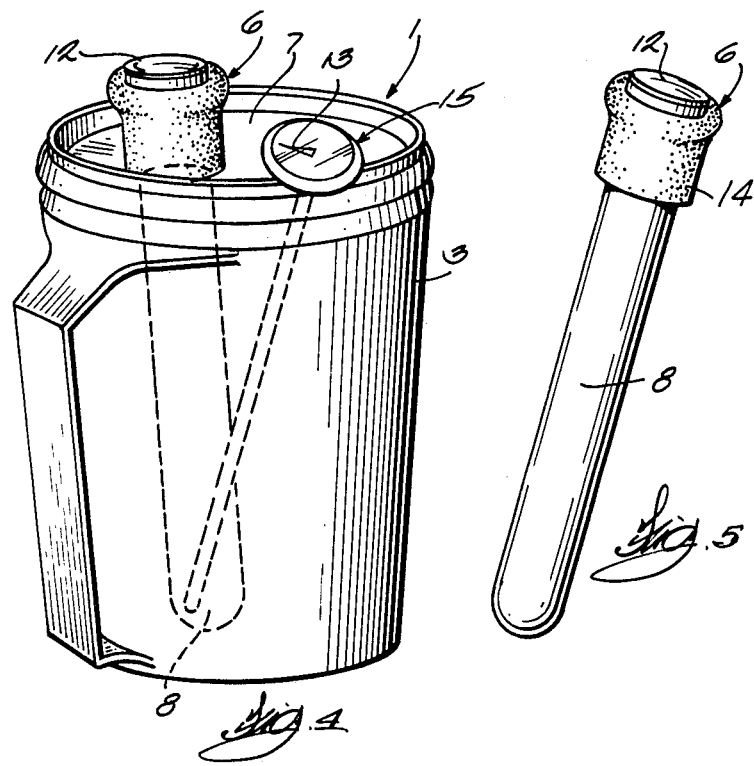
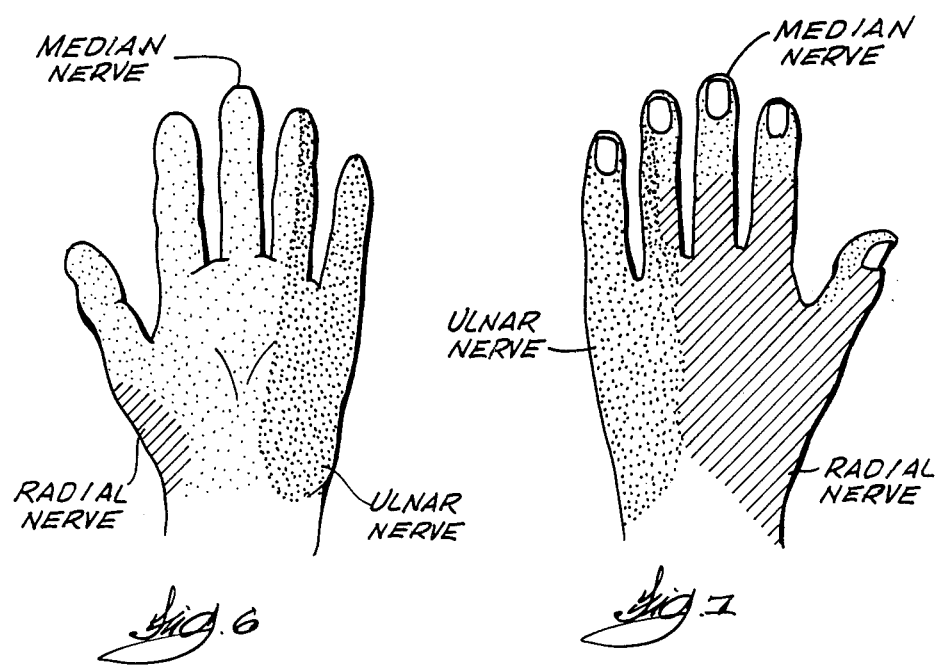

HOT AND COLD SENSOR DISCRIMINATION UNIT

BACKGROUND OF THE INVENTION

This invention relates to a diagnostic tool and, more particularly, to a hot and cold sensor unit having an insulated liquid-filled container with a thermometer to indicate the liquid temperature and a metallic probe with an integral temperature indicator for indicating the temperature of the probe.

Through neurologic examination of a patient with an injured spine, the localization of injury can sometimes be determined by the innervation of dermatomes. Evaluation of patients with cervical spine lesions can be accomplished by sensor-perception of probes of various temperatures. A thorough knowledge of the underlying anatomy and physiology of the nervous system is necessary for interpretation of the neurologic findings in cervical spine lesions. A neurological examination requires accurate observation and recording in conjunction with a detailed neurological history. Localizing of the cervical spine lesions may be accomplished—at least in part—through temperature-sensory probes applied to the different surfaces of the skin of the patient. Innervation of the areas of the body are controlled through nervous energy from the nervous system. The dermatomes are controlled by nerves associated with specific cervical openings in the cervical spine. Lesions at these points will cause abnormal or even lack of perception of temperature by the patient.

Accordingly, localization of the cervical spine lesion requires a thorough familiarity not only with the cross sectional anatomy, but also with the details of the longitudinal axis. In general, the higher the lesion in the cervical spinal canal, the greater the loss in motor, sensory and autonomic function. A high complete transection of the cervical cord results in complete quadriplegia with respiratory impairment and is usually fatal. Lesions that involved multiple segments of the cervical cord and are incomplete may give rise to upper and lower motor neuron signs and long tract sensory and autonomic disturbance to a variable degree.

The neurological assessment of patients with suspected cervical spinal pathology must be accompanied by a general physical examination.

The sensory and motor supply of each cervical nerve root differs from that of a peripheral nerve in the upper limbs. A variable number of cervical nerve roots contribute to the formation of a peripheral nerve.

Sensory symptoms following cervical root compression or irritation involve the specific dermatome distribution. There is a slight overlap so that complete anaesthesia usually occurs when two or more posterior nerve roots have been interrupted.

Accordingly, a means for determining the perception of heat and cold has been devised to give some indication for localizing the lesion in the cervical spine. The applicants have provided for a diagnostic tool in which the temperature of the probe is controlled in providing a means for determining innervation of dermatome distribution.

The patient is put in a non-distracting environment and the probes are applied at various points on the forearm. The perception of the patient to application of the probes at various points on the forearm is sensed and recorded.

Accordingly, it is an object of this invention to provide a diagnostic tool for determining perception of multi-temperature probes applied to the skin surface to determine innervation and the dermatomic distribution. The perception will determine abnormal or lack of innervation of the surfaces treated.

It is a further object of this invention to provide a multiple number of probes, each of a different temperature, to sense differential of temperature perception of the patient as applied to various surfaces on the body. Temperature perception is recorded for determination of location of cervical spine lesions.

SUMMARY OF THE INVENTION

The objects of this invention are accomplished with the use of a diagnostic tool including essentially an insulated container for reception of a liquid. The liquid is maintained at a predetermined temperature and the temperature is indicated by a thermometer extending into the fluid body. Also inserted in the fluid body are at least one probe consisting of a heavy metallic tube to retain heat. The probe also includes a thermometer to visually indicate the temperature of the probe.

An insulating cap is provided for a handle on the probe so that the clinician will not burn his hand or be uncomfortable when testing the patient.

A number of containers are used and each container will contain a liquid of a different temperature to thereby provide a means for perception of a differential of temperatures when testing the patient.

Referring to the drawings, the preferred embodiment of this invention is illustrated.

FIG. 1 illustrates a cross sectional view of the container containing a body of liquid and the probe therein;

FIG. 2 is a cross section view of the probe showing the thermometer in the metallic probe and the insulating cap;

FIG. 3 is an end view of the thermometer for indicating temperature in the probe;

FIG. 4 is a three-dimensional view of the container, the probe and thermometer;

FIG. 5 is a three-dimensional view of the probe;

FIGS. 6 and 7 illustrate the dermatome distribution of the nerve endings for innervation of the hand.

DESCRIPTION OF THE PREFERRED EMBODIMENTS

Referring to FIG. 1, the container 1 includes an inner wall 2 and an outer wall 3 forming a chamber containing the insulated material 4. The container 1 receives the liquid 5 which is held at a predetermined temperature. The probe 6 is inserted in a perforation in the cover 7. The cover 7 snaps into place and is retained on the top of the container 1.

FIG. 2 illustrates the probe 6 which consists essentially of a tube 8, preferably constructed of aluminum and having a thick wall. The metal wall has substantial heat capacity and is a good conductor and so provides a good probe and a relatively constant temperature of the probe while it is being used.

The thermometer 9 consists of a stem 10 extending into the hollow opening 11 of the tube 8. The thermometer 9 is screwed into the upper end of the tube 8 and forms an integral structure with the tube.

The dial 12 on the face, as indicated in FIG. 3, has a needle 13 to indicate the temperature in accordance with the numbered degrees as shown on the face of the thermometer.

The cap 14 is preferably constructed of a foam rubber and provides a handle for the probe to prevent the temperatures of the probe from being uncomfortable to the clinician who is operating the tests.

FIG. 4 illustrates a three-dimensional view of the container 1, probe 6 and thermometer 15. In this assembly the thermometer 15 provides a reading for the liquid within the container 1, so that the clinician can get an accurate determination of the temperature of the probe and the perception of temperatures by the patient. The probe—which is normally retained within the container—can be easily withdrawn from the container whenever it is desired to use the probe.

FIG. 5 illustrates the probe in a three-dimensional view.

FIGS. 6 and 7 show the dermatome distribution of nerve endings in the hand. The dermatome distribution provides a means for sensing a particular nerve and this will indicate the portion of the cervical spine where the lesions are and will assist the clinician in caring for the injury.

The neurologist or clinician is concerned with sensation, primarily for diagnostic purposes. A contribution which sensory examination may make to diagnosis depends upon the observation of certain forms of sensation which are appreciated less than normally, or not at all, also the demarcation of the area over which the impairment of the sensation is found.

The observation that apart from, or in addition to, impairment of sensation, the response to a sensory stimulus may be in other respects abnormal. The modes of sensibility which are tested are therefore those which are found to be of value in diagnostic purposes.

The test is provided to determine the patient's ability to discriminate between extremes of hot and cold and to detect variations in temperature at different levels. Four different levels are considered probably adequate.

An undisturbed and non-distracting atmosphere is provided for the patient who is seated comfortably at a table with both hands and forearms resting on the table. If four probes are used, one is filled with cold water, one with tepid water, one with warm water and one with hot water. Preferably a color code is used on the probes so that the neurologist readily knows which tubes he is using and what is the temperature, so that this can be recorded. The neurologist then touches the probe to the patient's palm or fingertips and the reception of the temperatures is recorded.

The patient is also asked to hold the probes and to determine from a sense of feeling, which ones are hot or cold, warm or tepid temperatures. The sensitivity of the patient in sensing the various temperatures of the probes is recorded and also the areas of the patient's hands and forearm is recorded in the diagnosis. This provides a measure of the normality of the nervous system to various temperatures of hot and cold. This not only provides an indicator as to the nerves which are injured, but also a a degree of localizing the lesion of the cervical spine causing the lack of perception for normal operation of the patient's nervous system.

The embodiment of the invention in which an exclusive privilege or property is claimed is defined as follows:

1. A diagnostic tool in the form of a kit for perception of temperatures on a sensory surface of the body, comprising:

an insulated container having a top and containing a liquid of predetermined temperature;

a cover fastened to the top of said container and forming perforations therethrough;

at least one probe extending through a perforation in said cover and into the liquid in said container;

a thermometer extending through another of the perforations of said cover and extending into the liquid of said container for sensing the liquid temperature, said probe including a metallic tube having an open top and a closed sensory end, means defining an opening extending from the top of the tube to the closed sensory end, a thermometer received in said tube opening and extending to the sensory end for sensing temperature of the tube, and a cap on the top of said probe providing a handle for holding said probe.

2. A diagnostic tool for perception of temperatures as set forth in claim 1, wherein said cap includes a foam rubber material.

3. A diagnostic tool for perception of temperatures as set forth in claim 1, including a second container and probe to thereby provide a plurality of probes, a liquid body in said second container of a different temperature from the liquid of the first container to thereby provide plural temperature sensing by said probes.

4. A diagnostic tool for perception of temperatures as set forth in claim 1, wherein said probe includes an integral structure of said thermometer, said tube and said cap.

5. A diagnostic tool for perception of temperatures as set forth in claim 1, comprising at least one additional container and probe, a liquid contained in said second container of a higher temperature than the liquid contained in the original container, to thereby provide plural temperature sensing by said probes.

6. A diagnostic tool for perception of temperatures as set forth in claim 1, including an additional container and probe, liquid of a different temperature contained in said second container, and a color coding on each of said probes to indicate the temperature of the probe for diagnostic sensing.

7. A diagnostic tool for perception of temperatures, comprising:

an insulated container having an upper end and receiving a liquid of predetermined temperature; a perforated cover on said container;

a thermometer extending into the liquid in said container for determining the liquid temperature;

a probe extending through said cover into the liquid of the container, said probe including a hollow metallic tube for conduction of heat through said tube, said tube defining an opening essentially the length of the tube, a thermometer extending into said opening in said tube for sensing the temperature of the probe, and said tube having a closed sensory end for sensing external temperature, and an insulating cap embracing an upper end of said tube providing an insulated handle for holding the probe.

8. A diagnostic tool for perception of temperatures as set forth in claim 7, wherein said probe includes a thick-walled aluminum tube for receiving said thermometer.

9. A diagnostic tool for perception of temperatures as set forth in claim 7, wherein said cap includes a material to form a padded cap on said probe.

10. A diagnostic tool for perception of temperatures as set forth in claim 7, wherein each of said thermometers includes a dial on the top to indicate temperatures.

11. A diagnostic tool for perception of temperatures on a sensory surface of the body, comprising:
   a closed insulated container for reception of liquid of a predetermined temperature;
   means defining perforations in an upper portion of said container;
   a thermometer received in a perforation of said container and extending into the liquid of said container for sensing the temperature of the liquid;
   a probe extending through a perforation in said container, said probe including
      a heavy-walled aluminum tube defining a central opening extending essentially the length of said tube and having a closed sensory end,
      said tube providing high heat capacity and good thermo conductivity,
   a thermometer extending into the central opening of said tube and extending to the closed end for indicating the temperature of the probe, and
   an insulated cap embracing an upper end of said probe providing a handle for said probe.

* * * * *